United States Patent [19]
Oka et al.

[11] Patent Number: 5,645,846
[45] Date of Patent: Jul. 8, 1997

[54] METHOD OF DISINFECTING AN OBJECT AND ANTIVIRAL DISINFECTION LIQUID THEREFOR

[75] Inventors: Hiroaki Oka, Yawata; Toshikazu Tomioka, Ibaraki; Katsumi Tomita, Hirakata; Kenji Hoshino, Takatsuki; Atsushi Nishino, Neyagawa; Shigeharu Ueda, Suita, all of Japan

[73] Assignee: Matsushita Electric Industrial Co., Ltd., Osaka, Japan

[21] Appl. No.: 582,786

[22] Filed: Jan. 4, 1996

Related U.S. Application Data

[62] Division of Ser. No. 420,182, Apr. 11, 1995, Pat. No. 5,516,519, which is a division of Ser. No. 134,124, Oct. 8, 1993, Pat. No. 5,429,819.

[30] Foreign Application Priority Data

| Oct. 14, 1992 | [JP] | Japan | 4-275706 |
| Dec. 28, 1992 | [JP] | Japan | 4-348113 |
| Jan. 19, 1993 | [JP] | Japan | 5-006410 |

[51] Int. Cl.[6] .................................................. A61K 9/16
[52] U.S. Cl. ........................ 424/405; 424/408; 424/409
[58] Field of Search .......................... 424/405, 408, 424/409, 711, 618, 637, 641

[56] References Cited

U.S. PATENT DOCUMENTS

| 3,007,844 | 11/1961 | Schulz | 424/711 |
| 3,079,213 | 2/1963 | Mendelsohn et al. | 424/641 |
| 3,527,596 | 9/1970 | Butterfield | 424/641 |
| 4,220,661 | 9/1980 | Huitson | 424/711 |
| 4,289,758 | 9/1981 | Van Leuven | 424/75 |
| 4,309,451 | 1/1982 | Vidal et al. | 424/711 |
| 4,378,351 | 3/1983 | Petrovich | 424/711 |
| 4,474,759 | 10/1984 | Petrovich | 424/711 |

FOREIGN PATENT DOCUMENTS

| 0488269 | 6/1992 | European Pat. Off. |
| 59-222405 | 12/1984 | Japan |
| 4231063 | 8/1992 | Japan |
| 91204169 | 2/1993 | Japan |
| 92064576 | 10/1993 | Japan |
| 0965010 | 7/1964 | United Kingdom |

OTHER PUBLICATIONS

Chemical Abstracts Service CA:97(21):174528w of Y.F. Borisovich et al., "Antiviral and Toxic Properties of Silver Thiosulfate Complexes," *Tr.–Vses. Gos. Nauchno–Kontrol'n. Inst. Vet. Prep.* (1980) 29–30:127–32.
European Search Report dated Feb. 4, 1994 regarding European Patent Application No. EP 93 11 6576.5, 4 pages.

*Primary Examiner*—Thurman K. Page
*Assistant Examiner*—Sharon Howard
*Attorney, Agent, or Firm*—Panitch Schwarze Jacobs & Nadel, P.C.

[57] ABSTRACT

An antiviral composition comprising: a thiosulfate salt and at least one of thiosulfate complex salt of a metal and a porous particulate carrier; said metal being at least one selected from the group consisting of silver, copper and zinc: said salts being carried on said porous particulate carrier. It is applicable to a wide range of living environment such as medical instruments and appliances, hygienic implements as well as kitchen utensils, and also demonstrates an antibacterial activity in addition to the antiviral activity. The composition releases its salts slowly to the environment and the antiviral and antibacterial activities of said composition lasts for a long period of time. A method for preparing said composition as well as an antiviral disinfection method and a virucidal disinfection fluid using said composition are also disclosed.

4 Claims, 5 Drawing Sheets

METHOD OF DISINFECTING AN OBJECT AND ANTIVIRAL DISINFECTION LIQUID THEREFOR

CROSS-REFERENCE TO RELATED APPLICATIONS

This is a division of U.S. patent application Ser. No. 08/420,182, filed Apr. 11, 1995, now U.S. Pat. No. 5,516,519, which is a division of U.S. patent application Ser. No. 08/134,124, filed Oct. 8, 1993, now U.S. Pat. No. 5,429,819.

FIELD OF THE INVENTION AND RELATED ART STATEMENT

1. Field of the Invention

The present invention relates to an antiviral composition which is applicable to a wide range of living environment such as medical instruments and appliances, hygienic implements as well as kitchen utensils.

Said antiviral composition also demonstrates an antibacterial activity in addition to the antiviral activity. Further, it is concerned with an antiviral and antibacterial disinfection method, as well as any product comprising said composition.

2. Description of the Related Art

Heretofore, there have been various chemotherapeutic agents such as 1-adamantanamine hydrochloride salts, thiosemicarbazide, arabinocyl nucleotide, 2',3'-dideoxynucleotides, and derivatives of pyrphosphates, as an antiviral agent. In addition, there have been hygienic products such as condom which has been incorporated with a metal or metal salt of silver or copper as its antibacterial and antiviral agents.

Each of the above-mentioned antiviral agents is however effective only to a specified species of the virus, and does not have any antibacterial property. Thus, such antiviral agents cannot be utilized in a use other than pharmaceutical products. Further, there has since been no antiviral agent that can withstand the molding temperature of a resin and can thus be employed as an antiviral component to be incorporated into molded resin products. In the above-mentioned hygienic products which has been incorporated with the antibacterial and antiviral agents, the antibacterial and antiviral agents are directly mixed with the material for forming the products. Since these agents are directly incorporated into the products, it is inevitable for these antibacterial and antiviral agents to expose themselves from the surface of the products. And, the thus exposed agents are caused to directly contact a human body and to adversely stimulate his skin. In addition, the antibacterial and antiviral activities of these agents cannot be controlled in a manner that the amount of these agent actually participating in the antibacterial and antiviral action on the surface of these product is properly adjusted by any means.

OBJECT AND SUMMARY OF THE INVENTION

It is therefore a primary object of the present invention to provide an antibacterial and antiviral composition that can be applied to a resin molded product, a rubber molded product, a resinous textile and the like products as well as a pharmaceutical product.

It is another object of the present invention to provide an antibacterial and antiviral composition, whose component having antibacterial and antiviral activities does not directly expose itself from the surface of the carrier thereof, and which composition has a small skin stimulation even if the resin molded product incorporating the composition is made to be in contact with the human body.

It is a further object of the present invention to provide an antibacterial and antiviral composition having a slow releasing property, and thus maintaining its antibacterial and antiviral activities to be effective for a long period of time.

It is still another object of the present invention to provide an antibacterial and antiviral disinfection method.

According to the present invention, there is provided an antibacterial and antiviral composition comprising: a thiosulfate salt and at least one thiosulfate complex salt of a metal and a porous particulate carrier, said metal being at least one selected from the group consisting of silver, copper and zinc; said salts being carried on said porous particulate carrier.

A preferred antibacterial and antiviral composition of the present invention comprises: silver thiosulfate salt and silver thiosulfate complex salt which are carried on a porous particulate carrier.

In the above-mentioned antibacterial and antiviral composition, said porous particulate carrier includes particles of an inorganic oxide such as silica gel, alumina, zeolite, zirconia, montmorillonite, and the like, but the most preferred of these oxides is silica A preferred antibacterial and antiviral composition of the present invention is such that at least part of said porous particulate carrier which carries said thiosulfate complex salt and said thiosulfate salt is coated with a layer of a coating material.

In compliance with a covering area, thickness, porosity, and the like of said layer of the coating material, the degree and rate of releasing of the salt carried on said carrier are properly controlled.

A preferred material for said coating material layer is silicon dioxide, and as a method for forming said silicon dioxide layer, there is exemplified a sol-gel method of hydrolyzing an alcoholic solution of an alcoxysilane by adding water to the solution. A preferred alcoxysilane and alcohol have an alkyl group having 1–4 carbon atoms in their molecule.

By forming said coating material layer, the above-mentioned antibacterial and antiviral composition becomes to have a preferred slow releasing property. Therefore, it has a scarce detrimental effect for contaminating the environment. In addition, by the provision of the coating material layer, a heat stability of the metal salt, particularly of the silver salt, carried on the carrier is improved.

Although the above-mentioned thiosulfate metal salt and thiosulfate complex salt can hardly be obtained as a simple substance in a solid state, it is possible to prepare them as water-soluble compounds, to carry said compounds on a porous particulate carrier such as silica gel by impregnating the carrier with an aqueous solution of said compounds and to immobilize them by drying to a state of being carried on the carrier.

According to another aspect of the present invention there is provided a method for preparing the above-mentioned antiviral composition including the metal thiosulfate salt and at least one metal thiosulfate complex salt carried on the porous particulate carrier.

The above-mentioned thiosulfate metal salt and thiosulfate complex salt can be obtained first by adding a salt selected from the group consisting of sulfite salt and hydrogen sulfate salt to an aqueous solution of a salt of said metals, and then by adding a thiosulfate salt to said aqueous solution.

The proportions of said salts, to be added to said aqueous solution of the metal salt suitable for preparing said thiosulfate metal salt and thiosulfate metal complex salt, are approximately 2–4 moles of said sulfite salt and/or hydrogen sulfate salt and 2–6 moles of said thiosulfate salt for one mole of the metal salt. If the amounts of the sulfite salt and/or hydrogen sulfate salt and the thiosulfate salt are too small, the formation of the complex salt is not sufficient, but the too large amounts causes a discoloration of the obtained salt and complex salt.

Furthermore, it is preferable to use approximately 1–10, and more preferably 3–5 parts by weight of the total amount of the thiosulfate metal salt and the thiosulfate metal complex salt to be carried on the porous particulate carrier, for 100 parts by weight of the carrier. If the total amount is too large, the carried carrier becomes to be liable to discolor.

Each of said sulfite salt, hydrogen sulfate salt and thiosulfate salt is preferably a sodium salt, and more preferably a potassium salt.

The aqueous solution of the thiosulfate metal salt and the thiosulfate metal complex salt obtained in the above-mentioned manner can be employed as a bactericidal disinfecting solution having both the antibacterial and antiviral activities as it is.

According to another aspect of the present invention there is provided a method for disinfecting an object other than human body comprising: subjecting said object contaminated with virus to a contact with a solution containing the thiosulfate metal salt and the thiosulfate metal complex salt, and suppressing the growth of said virus. The object may include medical instruments appliances as well as hospital and nursing rooms.

A further preferable virucidal disinfection method is employing a dispersion of a porous particulate carrier, which carries thereon the thiosulfate metal salt and the thiosulfate metal complex salt in water, an alcohol or a mixed solution of water and an alcohol, as the virucidal disinfection solution. Since said carrier has a slow releasing property of the salt being carried thereon, the disinfecting solution demonstrates the antibacterial and antiviral activities which will last for a long period of time.

The total amount of said thiosulfate metal salt and the thiosulfate metal complex salt included in the above-mentioned virucidal disinfecting solution is preferably 1–10 g for 100 ml of said solution.

The thiosulfate metal salt and the thiosulfate metal complex salt are forming radicals near their molecules by an action of oxygen in the air, and the radicals exert an influence on the surface of a membrane of the microorganism which accesses to the radicals and thus The metal salts demonstrate the antibacterial and antiviral activities. That is, it is presumed that the metal salts exert their antibacterial and antiviral actions on the microorganisms by bonding said metal complex ion or metal ion to the surface of an envelope of the virus and/or a membrane of the bacteria, and the bound ions inhibit denucleus process of the virus and/or the growth of the bacteria. At the same time, these agents demonstrate their activities by means of an inhibition of DNA synthesis and an inhibition of transcriptase and/or reverse transcriptase in these microorganisms.

In the virucidal disinfecting solution, by employing ethanol as the solvent or the dispersant for the solution, an effect of immediately breaking a lipomembrane (phospholipid membrane) of the bacteria or the virus can be added to the virucidal and bactericidal action of the metal complex salt. It is therefore preferable to use a mixed solution of water/ethanol containing 20–70% by weight of ethanol. In addition, it is possible to use another disinfectant, and a preferred disinfectant is an aqueous solution containing an alkyldiamino ethylglycine hydrochloride in 20–40% by weight.

The thiosulfate complex metal salt and the thiosulfate metal salt of the present invention can be modified of their antibacterial and antiviral activity to a wider spectrum by employing together with various chemotherapeutic agents. Such chemotherapeutic agents can be exemplified as, for instance, 1-adamantine hydrochloride, thiosemicarbazide, arabinocyl nucleotide and 2',3'-deoxynucleotide.

As a method for employing the salts of the present invention with these chemotherapeutic agents there is a method of causing an aqueous solution of these agents to be carried on the porous particulate carrier together with the thiosulfate metal salt and the thiosulfate metal complex salt, or a method of mixing these agents with the porous particulate carrier which has already carried the thiosulfate metal salt and the thiosulfate metal complex salt thereon.

The antibacterial and antiviral composition of the present invention can give the antibacterial and antiviral activities on various resin products, rubber products, resinous textile product and the like, by mixing the composition in the material for forming the products. For instance, the silicone rubber which will be described later in Example 5 may be employed as a material for a contraceptive condom, and the water-absorbing powder which will be described later in Example 6 may be employed as a material for a menstrual blood absorber. In addition, by mixing the composition in an ointment base such as vaseline, an antiviral ointment may be obtained.

While the novel features of the present invention are set fourth particularly in the appended claims, the invention, both as to organization and content, will be better understood and appreciated, along with other object and features thereof, from the following detailed description taken in conjunction with the attached drawings.

DESCRIPTION OF THE PREFERRED EMBODIMENT

In the following paragraphs, preferred embodiments of the present will be described with reference to the attached drawings.

Property

The antibacterial and antiviral composition of the present invention comprises: a porous particulate carrier and thiosulfate salt and thiosulfate complex salt of silver, copper or zinc, carried on said carrier. The most preferred thiosulfate complex salt and thiosulfate salt are those of silver. A preferred carrier is silica gel having a mean particle diameter of 1–10 μm, and particularly is Type B silica gel particle defined in Japanese industrial Standard JIS Z 0701.

Particularly preferred silica gel is one that has a moisture absorption rate of 20% or below under a low humidity environment (relative humidity: 50% or below, 25° C.) and a moisture absorption rate of 50% under a high humidity environment (relative humidity: 90% or above, 25° C.). The silica gel does thus scarcely release moisture under the low humidity environment but release moisture in large quantity under the high humidity environment. The antibacterial and antiviral agents carried on such silica gel are hardly volatile and are stable to heat, and thus demonstrate their antibacterial and antiviral activities for a long period of time. Further, silica gel is generally transparent and its refractive index is similar to that of any synthetic resin. Therefore, when the silica gel carrying the antibacterial and antiviral agents is incorporated into the synthetic resin and the like, it does not change the color of the resin.

Preparation

A preferred antiviral composition of the present invention is prepared, for instance, in the following procedure. First, an aqueous solution of the silver thiosulfate and the silver thiosulfate complex salt is prepared by adding sodium sulfite and sodium thiosulfate to an aqueous solution of silver acetate. Then, a porous particulate carrier such as silica gel is impregnated with the thus obtained aqueous solution and is then dried, to immobilize the contained agents in the carried state.

Figure 1:
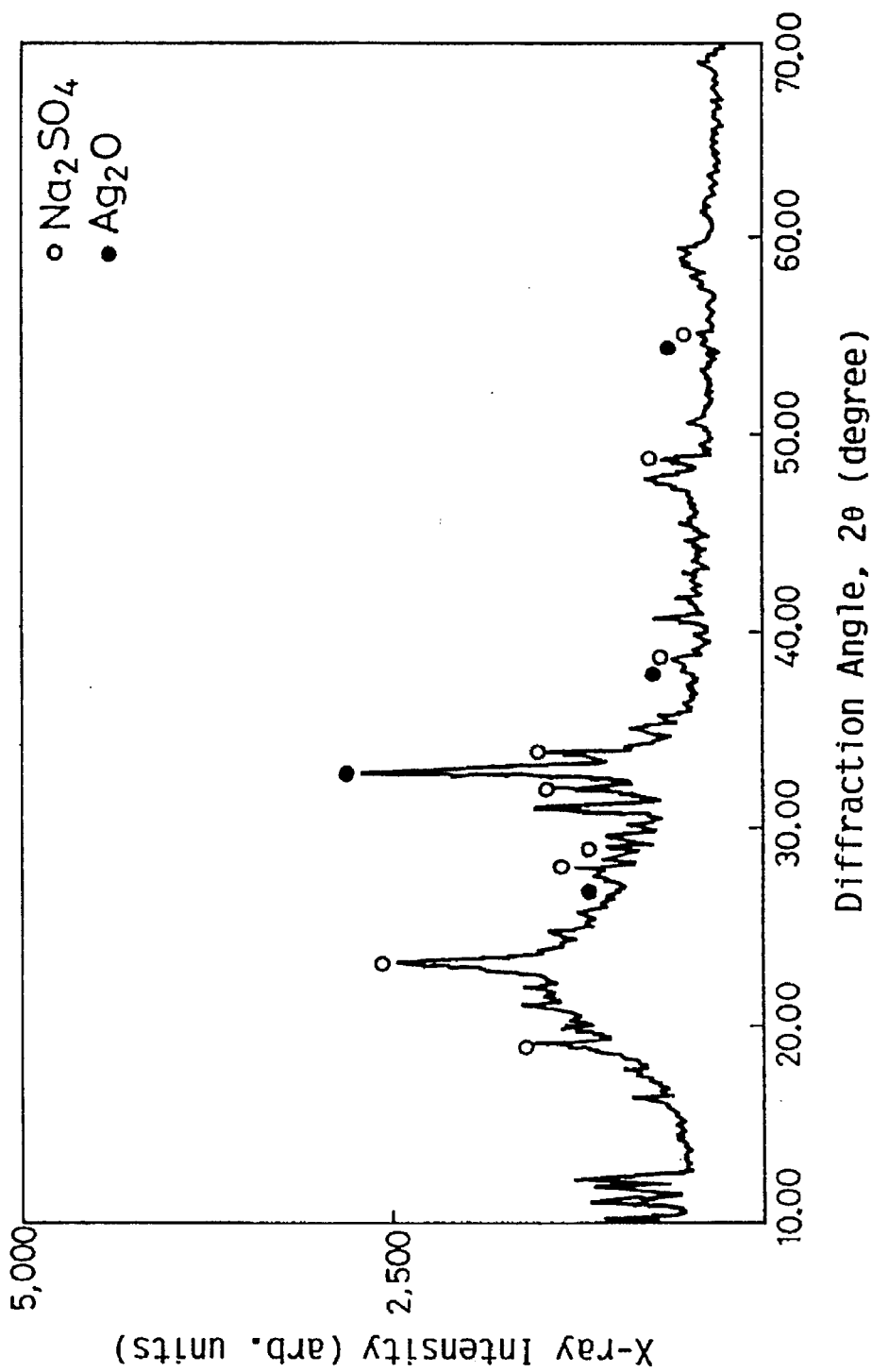
FIG. 1 is an X-ray diffraction pattern of the antiviral composition prepared in accordance with one embodiment of the present invention.

Although it is not apparent in what state are the above-mentioned silver salts being carried on the carrier, it is possible to identify the silver salts on the carrier by means of X-ray diffraction with a Kα line of Cu. FIG. 1 shows the X-ray diffraction pattern, and there is recognized diffraction lines of $Ag_2O$ (marked by ●), as well as power diffractions at 10.3°, 11.2°, 11.9° and 12.3° of the diffraction angle 2θ (hereinafter, these value of 2θ are referred to as $P_1$, $P_2$, $P_3$ and $P_4$, respectively) which are not recognized in the JCPDS (Joint Committee on Power Diffraction Standards) card. In this pattern, marks o show the diffraction lines of sodium sulfide ($Na_2SO_4$).

In the above-mentioned step of causing the silver salts to be carried on the carrier, if the drying temperature is raised, the X-ray power diffractions peculiar to the silver salts are made to disappear.

Figure 2:
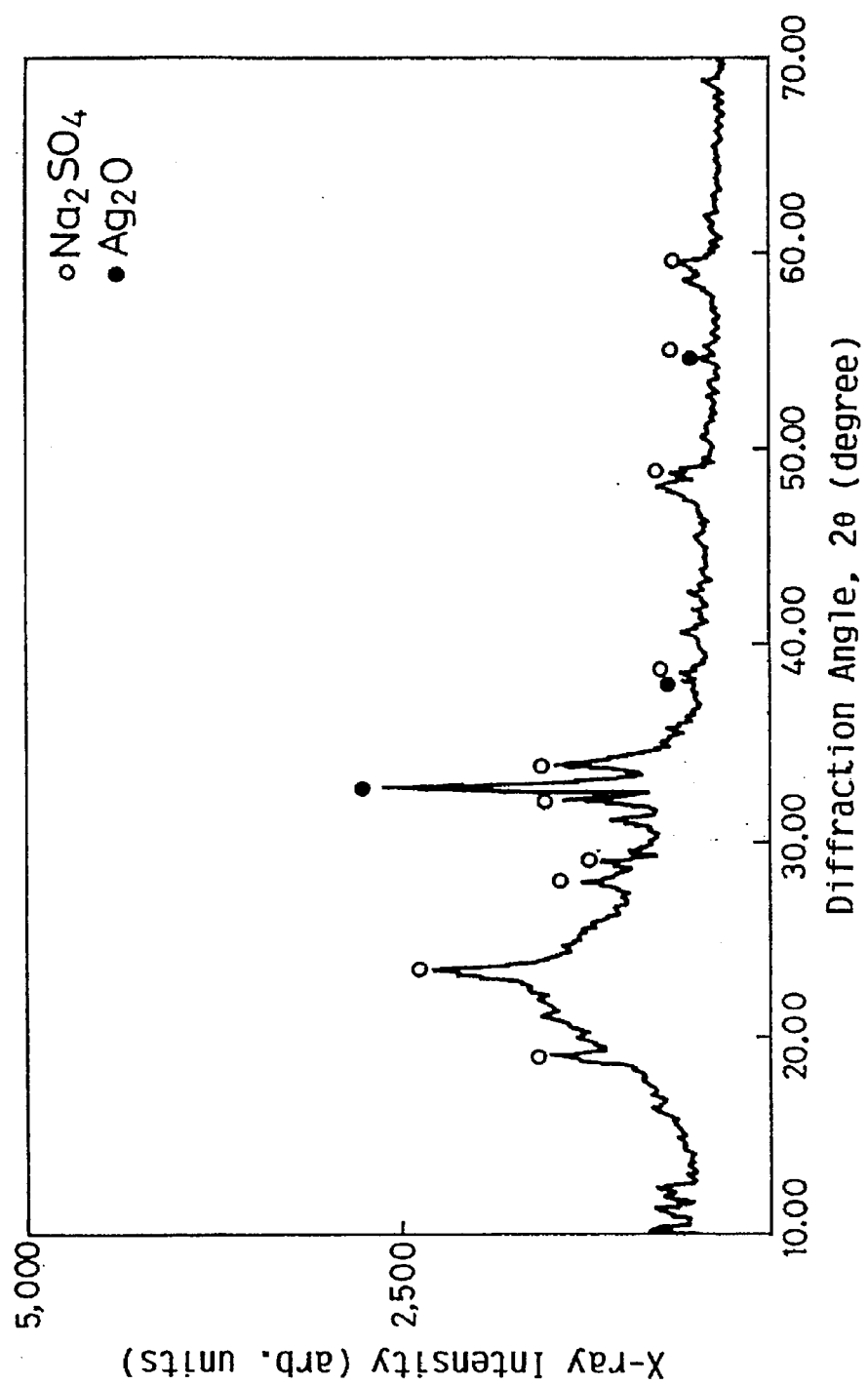
FIG. 2 is an X-ray diffraction pattern of the antiviral composition shown in FIG. 1 which has been heated at 240° C. for 10 minutes.
Figure 3:
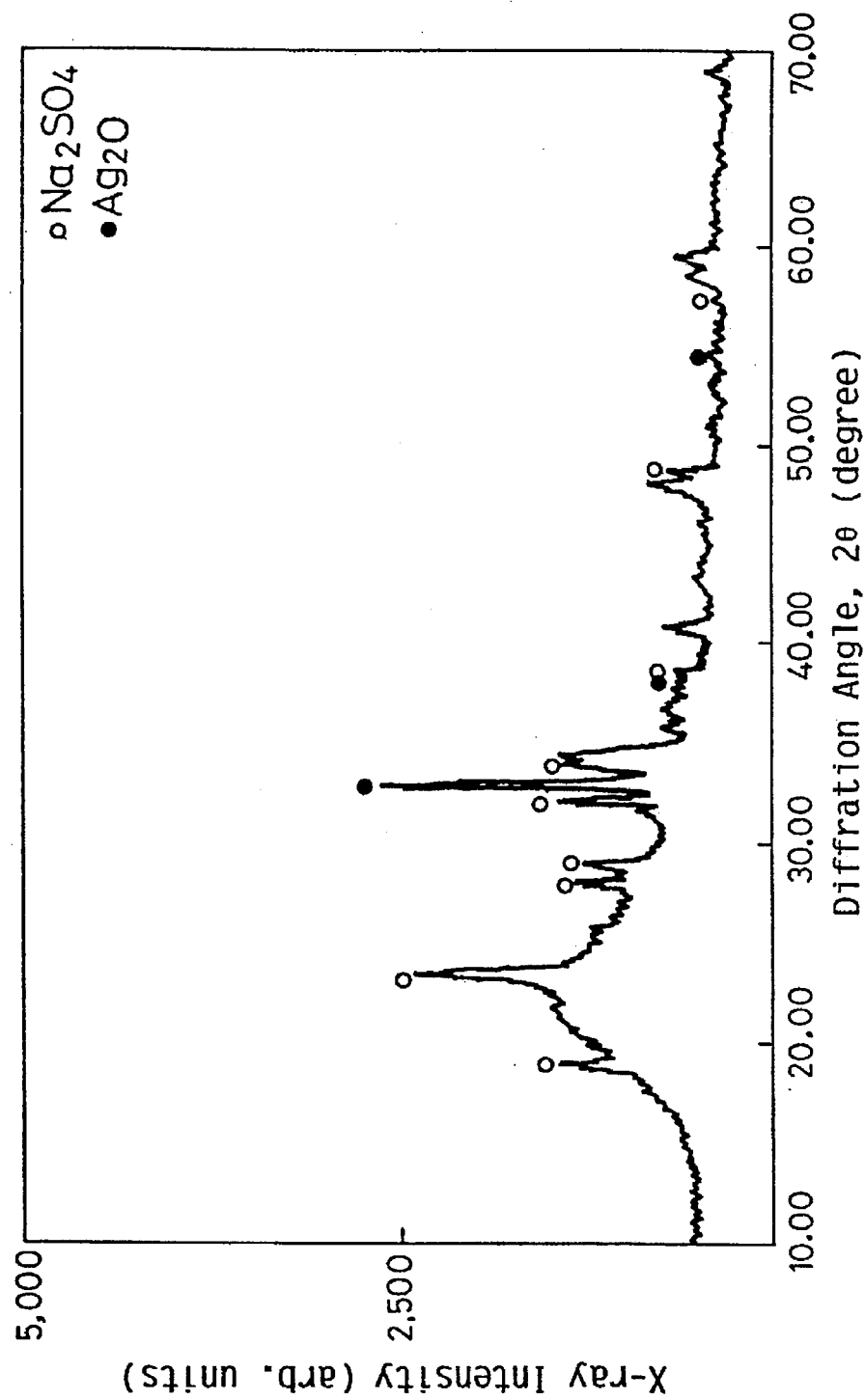
FIG. 3 is an X-ray diffraction pattern of the antiviral composition shown in FIG. 1 which has been heated at 240° C. for 30 minutes.
Figure 4:
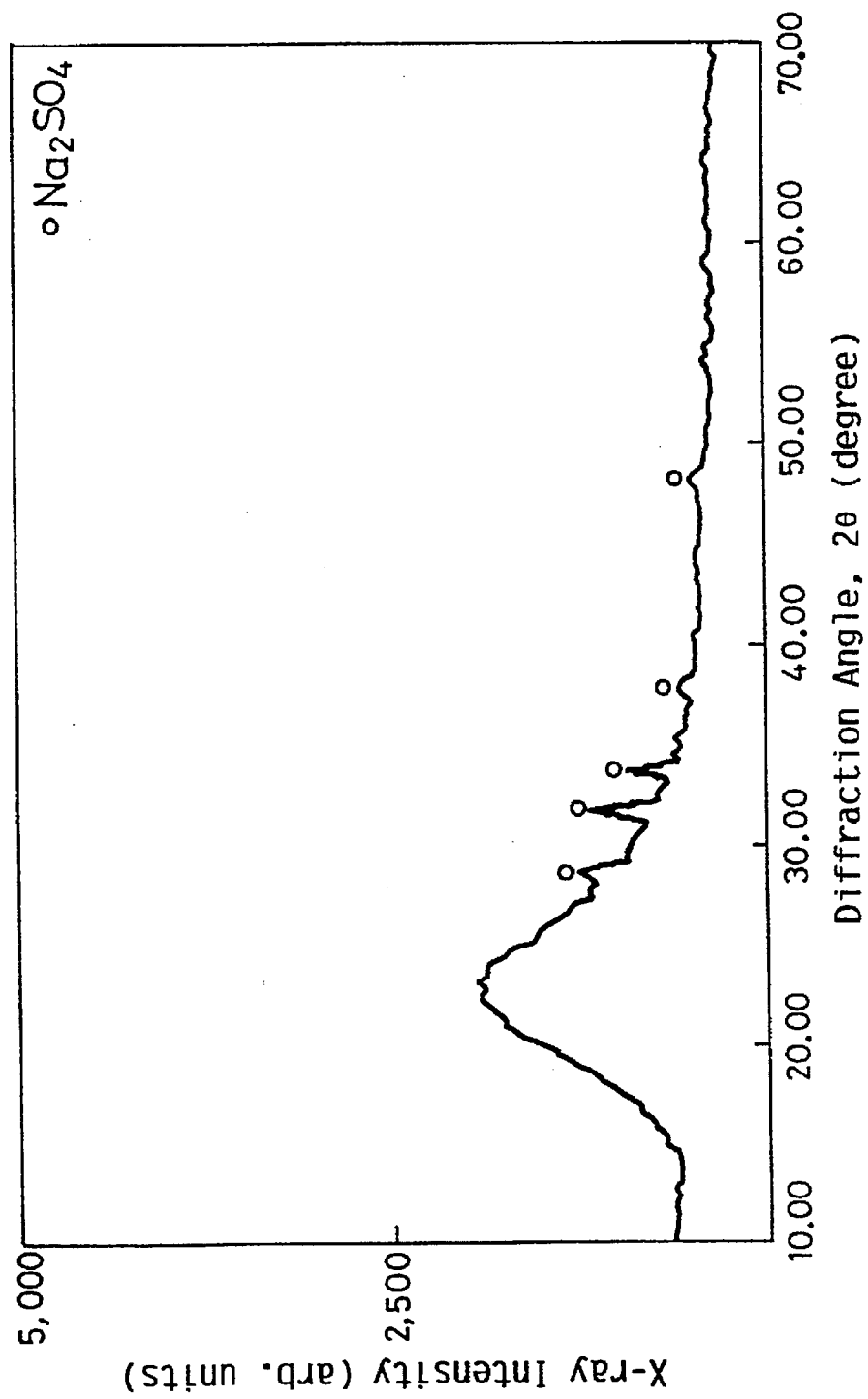
FIG. 4 is an X-ray diffraction pattern of the antiviral composition shown in FIG. 1 which has been heated at 500° C. for 5 minutes.

FIG. 1 shows the X-ray diffraction pattern of the antiviral composition obtained by the drying temperature at 100° C. or below. FIG. 2, FIG. 3 and FIG. 4 show the X-ray diffraction patterns of the antiviral composition obtained under the drying conditions at 240° C. for 10 min., at 240° C. for 30 min. and at 500° C. for 5 min., respectively.

When the drying temperature exceeds 200° C., the peaks of the diffraction lines of $Ag_2O$ and the power diffractions at $P_1$–$P_4$ gradually become small. And the antiviral composition which has subjected to a heat treatment at 500° C. demonstrates no power diffraction other than those of $Na_2SO_4$, because the silver compounds have presumably been sublimed out of the composition.

The composition that has an antibacterial and an antiviral activity as will be described later is those having small but distinct power diffractions at $P_1$–$P_4$ in the X-ray diffraction pattern as shown in FIG. 2, wherein all of the peaks of the power diffractions are approximately equal with one another, in addition to those having the X-ray diffraction pattern as shown in FIG. 1. The compositions having the X-ray diffractions patterns as shown in FIG. 3 and FIG. 4 have no antibacterial and antiviral activity.

Figure 5:
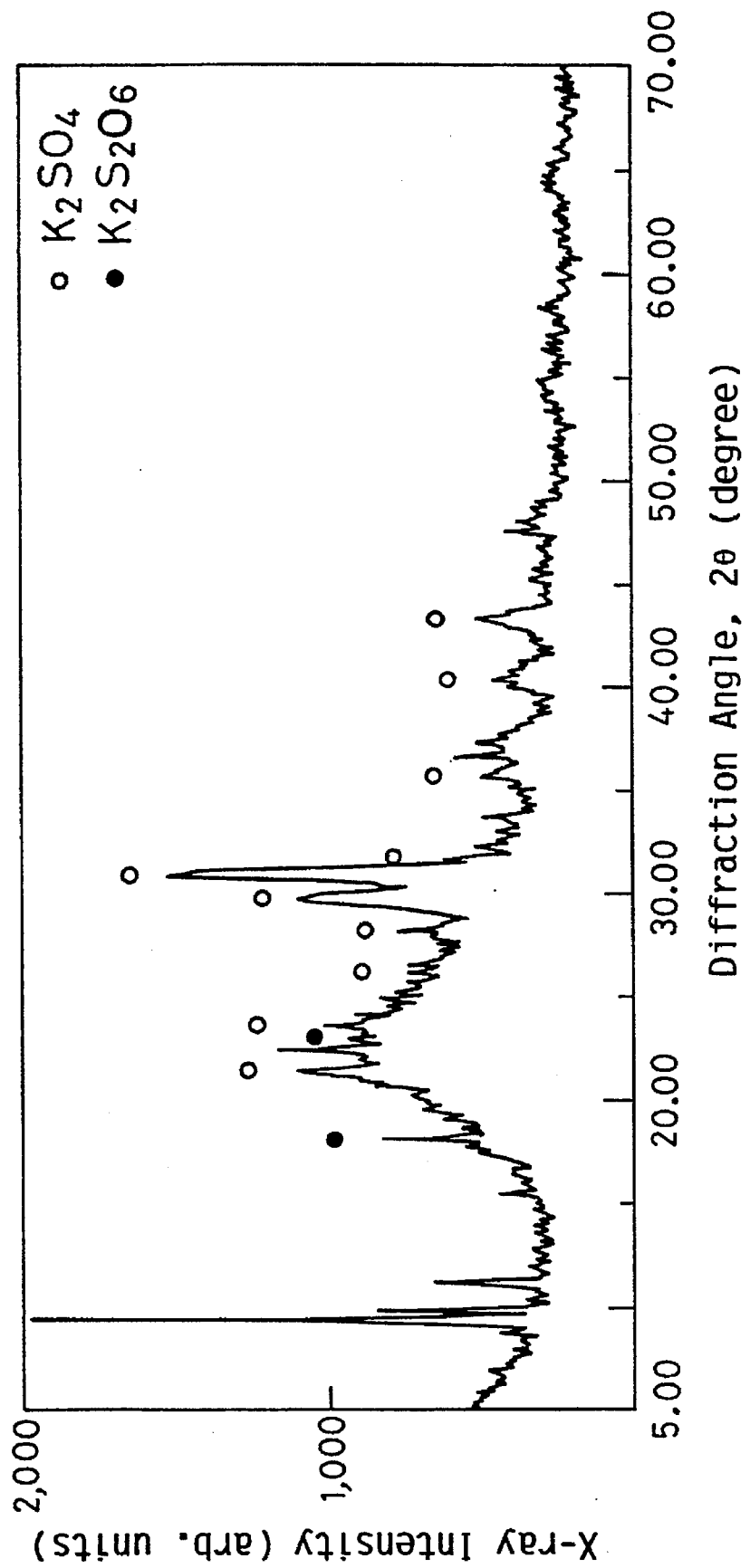
FIG. 5 is an X-ray diffraction pattern of the antiviral composition prepared in accordance with another embodiment of the present invention.

Although sodium salts such as sodium sulfite, hydrogen sulfate and thiosulfate are used in the above-mentioned preparation of silver thiosulfate complex salt and silver thiosulfate salt, a potassium salt may also be used in the preparation and an X-ray diffraction pattern of the composition obtained with the potassium salt is shown in FIG. 5. In this diffraction pattern, there is recognized peculiar power diffractions at 8.7°, 9.4°, 9.8° and 11.2° of the diffraction angle 2θ which are not recognized in the JCPDS card. As compared with that of FIG. 1, the diffraction pattern of FIG. 5 demonstrates that the diffraction angles representing the characteristic power diffractions are shifted to smaller angles. In this pattern, although diffraction lines of silver oxide ($Ag_2O$) are not clearly recognized but the diffraction lines representing potassium sulfate ($K_2SO_4$) and another potassium compound ($K_2S_4O_6$) are recognized.

As previously described, the silver thiosulfate complex salt and silver thiosulfate complex salt for being carried on the porous particulate carrier can be obtained by adding at least one salt selected from the group consisting of a sulfite salt and a hydrogen sulfate salt as well as a thiosulfate salt to an aqueous solution of a water-soluble silver salt such as silver acetate and silver nitrate. It is preferable to use from 2 moles to 4 moles of the sulfite salt and/or hydrogen sulfate salt, and from 2 moles to 6 moles of thiosulfate salt, for one mole of the silver salt.

In the thus obtained aqueous solution, silver thiosulfate complex ions represented by $[Ag(S_2O_3)]^{3-}$, $[Ag_2(S_2O_3)]^{2-}$, and the like, are existing together, in addition to thiosulfate ions and silver ions. In view of the fact that the aqueous solution does not produce any remarkable white turbid even when it is brought in contact with tap water containing chlorine, it is presumed that most of the silver ions are in a form of the complex ions. Anyway, in the above-mentioned coexisting state of the ions, the composition of the present invention demonstrates an antibacterial and antiviral activities.

In view of slow releasing and long acting property of the composition, it is preferable to select the amount of these silver thiosulfate salt and silver thiosulfate complex salt to be carried on the porous particulate carrier as 1–10 parts by weight, and more preferably as 2–5 parts by weight, for 100 part of the carrier.

EXAMPLE 1

Silver acetate (0.232 g) is dissolved in 30 ml of deionized water, and 0.627 g of potassium sulfite is added thereto and then stirred to dissolve therein. Thereafter, 1.54 g of potassium thiosulfate ($K_2S_2O_3$) is added to the mixture and stirred to dissolve. In this manner, an aqueous solution of silver thiosulfate salt and silver thiosulfate complex salt is prepared.

As a carrier for carrying the thus obtained aqueous solution, this Example employs a type B silica gel powder described in "JIS Z 0701: Silica Gel for packaging". This type B silica gel has a low moisture absorption rate under a low humidity environment, but it has a high moisture absorption rate under a high humidity environment, and therefor has a high total moisture absorption amount under the high humidity environment. In this Example, one that has a particle diameter of from 2 to 30 μm (average: 8 μm) is employed.

This type B silica gel powder is dried at 180° C. for 2 hours or longer, and further is dried at 60° C. for 24 hours.

Then, 100 parts by weight of the above-mentioned silica gel is mixed with the previously described aqueous solution containing its silver components in 2 part by weight, and the mixture is heated at 60° C. under a reduced pressure to remove its water component. Thereafter, the dried particles are pulverized to have a given particle diameter. In this way, the silica gel which carries the silver thiosulfate salt and the silver thiosulfate complex salt is obtained.

Next, 100 parts by weight of the above-mentioned silica gel is dispersed in a solution prepared by dissolving 100 parts by weight of tetraethoxysilane in 100 parts by weight of ethanol, and then the tetraethoxysilane in the obtained dispersion is hydrolyzed by adding pure water to cause silicon dioxide film as the hydrolyzed product of the tetraethoxysilane to coat at least part of the surface of the above-mentioned silica gel. Then, the coated silica gel is dried.

EXAMPLE 2

After dissolving 200 mg of silver acetate in 30 ml of pure water kept at 50°–60° C., the obtained solution is filtered to remove unsolved residue. To the filtrate, 1 g of potassium sulfite and 1.8 g of potassium thiosulfate are added in this order to be dissolved. To the obtained solution, a type B silica gel powder having a mean particle diameter of about 2.6 µm described in "JIS Z 0701: Silica Gel for packaging" is added to be mixed. Drying of this mixture under a reduced atmosphere gives a silica gel carrying the silver thiosulfate salt and the silver thiosulfate complex salt.

EXAMPLE 3

Cupric acetate (0.272 g) is dissolved in 30 ml of deionized water, and 1.0 g of potassium sulfite is added thereto to be dissolved. Next, 0.68 g of potassium thiosulfate ($K_2S_2O_3 \cdot 5H_2O$) is added to the obtained mixture to be dissolved and stirred. In this manner, an aqueous solution containing the cupric thiosulfate salt and the cupric thiosulfate complex salt is prepared.

Next, in a similar manner to that of Example 1, the cupric thiosulfate salt and the cupric thiosulfate complex salt are caused to be carried on silica gel and The part of the surface of the silica gel is coated with The silicon dioxide film.

EXAMPLE 4

Zinc acetate (0.286 g) is dissolved in 30 ml of deionized water, and 1.0 g of potassium sulfite is added Thereto to dissolve. Next, 0.66 g of potassium thiosulfate ($K_2S_2O_3 \cdot 5H_2O$) is added to the obtained mixture to dissolve and stirred. In this manner, an aqueous solution of the zinc Thiosulfate salt and the zinc thiosulfate complex salt is prepared.

Next, in a similar manner to that of Example 1, the zinc thiosulfate salt and the zinc thiosulfate complex salt are caused To be carried on silica gel and the part of the surface of the silica gel is coated with the silicon dioxide film.

EXAMPLE 5

The composition obtained by the procedure of Example 1, namely, the silica gel particles which carry the silver thiosulfate salt and the silver thiosulfate complex salt and whose surfaces are coated with the silicon dioxide film, is classified to have a particle diameter of 2 µm or smaller. The classified particles are then mixed with a material for silicone rubber in 3% by weight, and the obtained mixture is kneaded. The kneaded mixture is then molded into a given shape and thus caused to be bridged to obtain a thin film of silicone rubber.

EXAMPLE 6

Each 5 g of methyl acrylate and vinyl acetate are subjected to a process of suspension polymerization in 10 ml of benzene, and the polymerized product is dispersed in 10 ml of methanol. To this dispersion, 1 g of the silica gel carrying the silver thiosulfate salt and the silver thiosulfate complex salt which has been prepared in Example 2 is added. The Thus converted suspension is then saponified with an aqueous solution containing NaOH in 40% by weight and washed with acetone. The washed suspension is dried to remove its water component to obtain powder of water absorbing property.

EXAMPLE 7

An ointment is prepared by mixing the silica gel carrying the silver thiosulfate salt and the silver thiosulfate complex salt obtained in Example 2 in 3% by weight with an ointment base of vaseline.

EXAMPLE 8

L-adamantamine hydrochloride (10 mmol) is dissolved in the aqueous solution containing the silver thiosulfate salt and the silver thiosulfate complex salt which has been prepared by the process described in Example 1. The thus obtained aqueous solution is adsorbed on the silica gel particles employed in Example 2, and dried under reduced pressure.

EXAMPLE 9

Ten (10) grams of silica gel carrying the silver thiosulfate salt and the silver thiosulfate complex salt prepared in Example 2 is dispersed in 100 ml of an aqueous ethanol solution containing ethanol in 50% by weight to obtain a bactericidal disinfection solution.

EXAMPLE 10

Ten (10) grams of silica gel carrying the silver thiosulfate complex salt and the silver thiosulfate salt prepared in Example 4 is dispersed in 100 ml of an aqueous ethanol solution containing ethanol in 50% by weight to obtain a bactericidal disinfecting solution.

EXAMPLE 11

Another bactericidal disinfecting solution is prepared by standing the solution obtained in Example 9 at room temperature for a week.

Comparative Example 1

Another coating film of silicone rubber is prepared in a similar manner to those described in Example 5, but excluding the incorporation of the silica gel.

Comparative Example 2

Another bactericidal disinfecting solution is prepared by simply mixing water and ethanol by 50% by weight.

Comparative Example 3

Another bactericidal disinfecting solution is prepared by standing the solution obtained in Comparative example 2 at room temperature for a week.

Evaluation

In the following paragraph, the evaluation process performed on the antibacterial and antiviral activities of the samples prepared in accordance with the above-mentioned Examples and Comparative examples will be described.

Samples Subjected to the Evaluation

Each one gram of the products obtained by Examples 1–8 and Comparative example 1 and 3 ml of phosphate buffer solution are combined and stirred for 30 minutes, and salts contained in the product is extracted to give the samples for the evaluation. The disinfecting solutions obtained by Examples 9–11 and Comparative examples 2–3 are used as the samples as they are.

Virus Used in This Evaluation

Polio (Sabin alive Vaccine), Measles (Nagahata strain), Human immunodeficiency (AIDS) (JMH-1 strain), Helpes simplex (G strain), and influenza A virus (Okuda strain).

Bacteria Used in This Evaluation

*Escherichia coli, Staphylococcus aureus*, and Methicilline-resistant *Staphylocuccus aureus*.

Procedure

1. Antiviral Activity

Each one ml of the virus-containing solutions of TCID (Tissue Culture Infective Dose) $_{50}$(/ml): 6.5–8.5 is mixed with each one ml of the above-mentioned samples and stand still for 30 minutes. Then, the Vero cells derived from Kidney of the African green monkey (guenon), the MT—4 cells derived from the adult thymoctye leukemia patient and the MDCK cells derived from Kidney of Canien (each: $10^6$ cells/ml) are infected with each of the thus stood mixtures, and the infection activities are evaluated by state of the survival of the infected cells after a week, respectively. The results of this evaluation are summarized in Table 1.

TABLE 1

| | (antiviral activity) | | | | |
|---|---|---|---|---|---|
| Samples derived | $TCID_{50}$(/ml) [−log] virus | | | | |
| from | A | B | C | D | E |
| Example 1 | 9.0 | 2.0 | 2.5 | 1.5 | 2.5 |
| Example 2 | 9.0 | 2.0 | 2.5 | 2.5 | 2.5 |
| Example 3 | 9.0 | 3.5 | 4.0 | 3.0 | 3.5 |
| Example 4 | 9.0 | 3.5 | 4.0 | 3.0 | 3.5 |
| Example 5 | 9.0 | 2.5 | 3.0 | 3.0 | 3.5 |
| Example 6 | 9.0 | 2.5 | 3.0 | 3.0 | 3.5 |
| Example 7 | 9.0 | 2.5 | 3.0 | 3.0 | 3.5 |
| Example 8 | 9.0 | 1.0 | 1.0 | 1.0 | 1.0 |
| Example 9 | 2.5 | 0 | 0 | 0 | 0 |
| Example 10 | 2.5 | 0 | 0 | 0 | 0 |
| Example 11 | 9.0 | 2.0 | 2.5 | 2.5 | 2.5 |
| Comparative E. 1 | 8.5 | 7.0 | 6.5 | 8.5 | 6.5 |
| Comparative E. 2 | 4.0 | 4.0 | 3.5 | 4.0 | 3.5 |
| Comparative E. 3 | 8.0 | 7.0 | 6.5 | 6.5 | 6.5 |

A: Polio (Sabin alive vaccine), B: Measles (Nagahata strain), C: Human immunodeficiency (JMH-1), D: Helpes simplex (G strain), E: Influenza A virus (Okuda strain).

2. Antibacterial Activity

Each one ml of solutions containing the above-mentioned bacteria ($10^4$–$10^8$ CFU (colony forming units)/ml) is mixed with each one ml of the samples and stand still for 80 minutes. The stood mixtures are spread over normal agar media (available from Nissui Pharmaceutical K.K., Japan) with a dilution, respectively. The agar media are incubated for 18 hours, and numbers of the cells grown on the agar media after the incubation are counted for the evaluation. The results of this evaluation are summarized in Table 2.

TABLE 2

| | (antibacterial activity) | | |
|---|---|---|---|
| Samples derived | CFU/ml | | |
| from | E. coli | S. aureus | MRSA |
| Example 1 | 0 | 0 | 0 |
| Example 2 | 0 | 0 | 0 |
| Example 3 | 0 | 0 | 0 |
| Example 4 | 0 | 0 | 0 |
| Example 5 | 0 | 0 | 0 |
| Example 6 | 0 | 0 | 0 |
| Example 7 | 0 | 0 | 0 |
| Example 8 | 0 | 0 | 0 |
| Example 9 | 0 | 0 | 0 |
| Example 10 | 0 | 0 | 0 |
| Example 11 | 0 | 0 | 0 |
| Comparative E. 1 | $1.5 \times 10^5$ | $1.0 \times 10^4$ | $1.0 \times 10^4$ |
| Comparative E. 2 | 10 | 10 | 10 |
| Comparative E. 3 | $1.0 \times 10^4$ | $1.0 \times 10^4$ | $1.2 \times 10^3$ |

Although the present invention has been described in terms of the presently preferred embodiments, it is to be understood that such disclosures are not to be interpreted as limiting. Various alterations and modification will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A method for disinfecting a non-human object comprising: subjecting said object contaminated with virus to contact with an antiviral solution of a thiosulfate salt and at least one thiosulfate complex salt of at least one metal selected from the group consisting of silver, copper and zinc in water, an alcohol or a mixed solution of water and an alcohol, and suppressing growth of said virus.

2. The method in accordance with claim 1, wherein the total amount of said thiosulfate salt and thiosulfate complex salt is 1–10 grams for 100 ml of the solution.

3. An antiviral disinfection liquid comprising: a solution of a thiosulfate salt and at least one thiosulfate complex salt of at least one metal selected from the group consisting of silver, copper and zinc in water, an alcohol or a mixed solution of water and an alcohol.

4. The antiviral disinfection liquid in accordance with claim 3, wherein the total amount of said thiosulfate salt and thiosulfate complex salt is 1–10 grams for 100 ml of the solution.

* * * * *